United States Patent [19]

Smith

[11] 4,180,512

[45] Dec. 25, 1979

[54] PYRAN ANALOGS OF 4,5,13,14-TETRADEHYDRO-PGI$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 915,440

[22] Filed: Jun. 14, 1978

Related U.S. Application Data

[63] Continuation-in-part of Ser. No. 821,536, Aug. 3, 1977.

[51] Int. Cl.$^2$ .............................................. C07D 311/02
[52] U.S. Cl. ................................ 260/345.2; 542/426; 424/283
[58] Field of Search ........................ 260/345.2, 346.22; 542/426

[56] References Cited

PUBLICATIONS

Johnson et al., Prostaglandins, 12, 915 (1976).

*Primary Examiner*—Nicky Chan
*Attorney, Agent, or Firm*—Robert A. Armitage

[57] ABSTRACT

The present invention relates to certain novel pyran analogs of 4,5,13,14-tetradehydro-PGI$_1$ compounds wherein the C-5 to C-6 double bond of prostacyclin (PGI$_2$) is isomerized to the C-4 to C-5 position, the heterocyclic ring of PGI$_2$ is enlarged to 5 carbon atoms, and the C-13 to C-14 double bond is further unsaturated to a triple bond. These novel pyran analogs are useful as smooth muscle stimulators.

73 Claims, No Drawings

PYRAN ANALOGS OF 4,5,13,14-TETRADEHYDRO-PGI$_1$ COMPOUNDS

CROSS REFERENCE TO RELATED APPLICATION

The present application is a continuation-in-part application of Ser. No. 821,536, filed Aug. 3, 1977, now pending issuance as a U.S. patent.

The present invention relates to prostacyclin analogs, for which the essential material constituting disclosure therefor is incorporated by reference here from Ser. No. 821,541, filed Aug. 3, 1977, now U.S. Pat. No. 4,109,082, issued Aug. 22, 1978.

I claim:

1. A prostacyclin analog of the formula

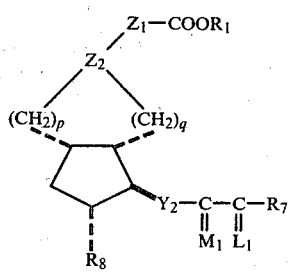

wherein Y$_2$ is —C≡C—;
wherein Z$_2$ is

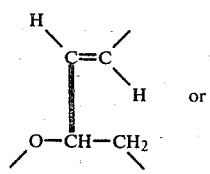 (1)

or

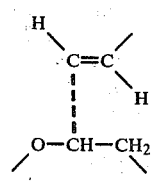 (2)

wherein one of p and q is one and the other is zero;
wherein Z$_1$ is
  (1) —(CH$_2$)$_g$—CH$_2$—CH$_2$—, or
  (2) —(CH$_2$)$_g$—CH$_2$—CF$_2$—,
  wherein g is the integer zero, one, or 2;
wherein R$_8$ is hydrogen, hydroxy, or hydroxymethyl;
wherein M$_1$ is

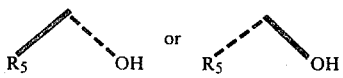

wherein R$_5$ is hydrogen or alkyl with one to 4 carbon atoms, inclusive,
wherein L$_1$ is

or a mixture of

and

wherein R$_3$ and R$_4$ are hydrogen, methyl, or fluoro, being the same or different, with the proviso that one of R$_3$ and R$_4$ is fluoro only when the other is hydrogen or fluoro;

wherein R$_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

 (a)

 (b)

 (c)

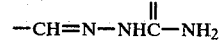 (d)

wherein R$_{25}$ is methyl, phenyl, acetamidophenyl, benzamidophenyl, or —NH$_2$; R$_{26}$ is methyl, phenyl, —NH$_2$, or methoxy; and R$_{27}$ is hydrogen or acetamido; phenacyl; phenacyl substituted in the para position by chloro, bromo, phenyl, or benzamido; or a pharmacologically acceptable cation;

wherein R$_7$ is

 (1)

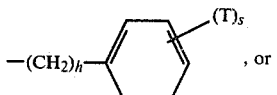 (2)

, or

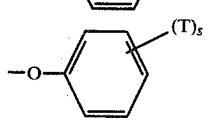 (3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein p is one.

3. A prostacyclin analog acording to claim 2, wherein $R_8$ is hydroxymethyl.

4. 11-Deoxy-11α-hydroxymethyl-trans-4,5,13,14,-tetradehydro-(6S)-9-deoxy-6,9α-epoxymethylene-PGF$_1$, a prostacyclin analog according to claim 3.

5. A prostacyclin analog according to claim 2, wherein $R_8$ is hydrogen.

6. 11-Deoxy-trans-4,5,13,14-tetradehydro-(6S)-9-deoxy-6,9α-epoxymethylene-PGF$_1$, a prostacyclin analog according to claim 5.

7. A prostacyclin analog according to claim 2, wherein $R_8$ is hydroxy.

8. A prostacyclin analog according to claim 7, wherein $Z_2$ is a mixture of

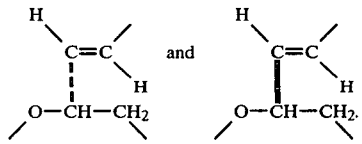

9. Trans-4,5,13,14-tetradehydro-(6RS)-9-deoxy-6,9α-epoxymethylene-PGF$_1$, a prostacyclin analog according to claim 8.

10. A prostacyclin analog according to claim 7, wherein $Z_2$ is

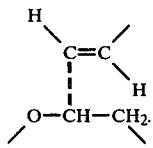

11. Trans-4,5,13,14-tetradehydro-(6S)-9-deoxy-6,9α-epoxymethylene-PGF$_1$, a prostacyclin analog according to claim 10.

12. 15-Methyl-trans-4,5,13,14-tetradehydro-(6S)-9-deoxy-6,9α-epoxymethylene-PGF$_1$, a prostacyclin analog according to claim 10.

13. 16,16-Dimethyl-trans-4,5,13,14-tetradehydro-(6S)-9-deoxy-6,9α-epoxymethylene-PGF$_1$, a prostacyclin analog according to claim 10.

14. 16,16-Difluoro-trans-4,5,13,14-tetradehydro-(6S)-9-deoxy-6,9α-epoxymethylene-PGF$_1$, a prostacyclin analog according to claim 10.

15. A prostacyclin analog according to claim 7, wherein $Z_2$ is

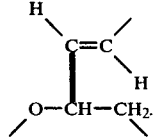

16. A prostacyclin analog according to claim 15, wherein $Z_1$ is —(CH$_2$)$_g$—CH$_2$—CF$_2$—.

17. 2,2-Difluoro-trans-4,5,13,14-tetradehydro-(6R)-9-deoxy-6,9α-epoxymethylene-PGF$_1$, a prostacyclin analog according to claim 16.

18. A prostacyclin analog according to claim 15, wherein $Z_1$ is —(CH$_2$)$_g$—CH$_2$—CH$_2$—.

19. A prostacyclin analog according to claim 18, wherein g is zero.

20. A prostacyclin analog according to claim 19, wherein $R_7$ is

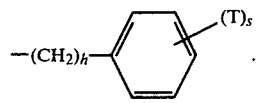

21. 17-Phenyl-18,19,20-trinor-trans-4,5,13,14-tetradehydro-(6R)-9-deoxy-6,9α-epoxymethylene-PGF$_1$, a prostacyclin analog according to claim 20.

22. A prostacyclin analog according to claim 19, wherein $R_7$ is

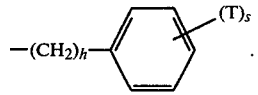

23. 16-Phenoxy-17,18,19,20-tetranor-trans-4,5,13,14-tetradehydro-(6R)-9-deoxy-6,9αepoxymethylene-PGF$_1$, a prostacyclin analog according to claim 22.

24. A prostacyclin analog according to claim 19, wherein $R_7$ is —(CH$_2$)$_m$—CH$_3$.

25. A prostacyclin analog according to claim 24, wherein m is 3.

26. A prostacyclin analog according to claim 25, wherein $R_5$ is methyl.

27. 15-Methyl-trans-4,5,13,14-tetradehydro-(6R)-9-deoxy-6,9α-epoxymethylene-PGF$_1$, a prostacyclin analog according to claim 26.

28. A prostacyclin analog according to claim 27, wherein $R_5$ is hydrogen.

29. A prostacyclin analog according to claim 28, wherein at least one of $R_3$ and $R_4$ is fluoro.

30. 16,16-Difluoro-trans-4,5,13,14-tetradehydro-(6R)-9-deoxy-6,9α-epoxymethylene-PGF$_1$, a prostacyclin analog according to claim 29.

31. A prostacyclin analog according to claim 28, wherein at least one of $R_3$ and $R_4$ is methyl.

32. 16,16-Dimethyl-trans-4,5,13,14-tetradehydro-(6R)-9-deoxy-6,9α-epoxymethylene-PGF$_1$, a prostacyclin analog according to claim 31.

33. A prostacyclin analog according to claim 28, wherein $R_3$ and $R_4$ are both hydrogen.

34. Trans-4,5,13,14-tetradehydro-(6R)-9-deoxy-6,9α-epoxymethylene-PGF$_1$, methyl ester, a prostacyclin analog according to claim 33.

35. Trans-4,5,13,14-tetradehydro-(6R)-9-deoxy-6,9α-epoxymethylene-PGF$_1$, tris(hydroxymethyl)amino methane salt, a prostacyclin analog according to claim 33.

36. Trans-4,5,13,14-tetradehydro-(6R)-9-deoxy-6,9α-epoxymethylene-PGF$_1$, adamantanamine salt, a prostacyclin analog according to claim 33.

37. Trans-4,5,13,14-tetradehydro-(6R)-9-deoxy-6,9α-epoxymethylene-PGF$_1$, a prostacyclin analog according to claim 33.

38. A prostacyclin analog according to claim 1, wherein q is one.

39. A prostacyclin analog according to claim 38, wherein $R_8$ is hydroxymethyl.

40. 11-Deoxy-11α-hydroxymethyl-trans-4,5,13,14-tetradehydro-7a-homo-6α-PGI$_1$, a prostacyclin analog according to claim 39.

41. A prostacyclin analog according to claim 38, wherein $R_8$ is hydrogen.

42. 11-Deoxy-trans-4,5,13,14-tetradehydro-7a-homo-6α-PGI$_1$, a prostacyclin analog according to claim 41.

43. A prostacyclin analog according to claim 38, wherein R$_8$ is hydroxy.

44. A prostacyclin analog according to claim 43, wherein Z$_2$ is a mixture of

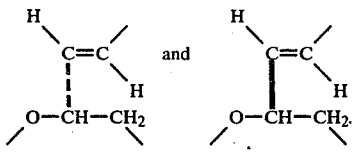

45. Trans-4,5,13,14-tetradehydro-(6RS)-7a-homo-PGI$_1$, a prostacyclin analog according to claim 44.

46. A prostacyclin analog according to claim 43, wherein Z$_2$ is

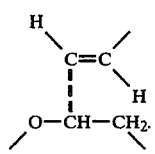

47. Trans-4,5,13,14-tetradehydro-7a-homo-6α-PGI$_1$, a prostacylcin analog according to claim 46.

48. 15-Methyl-trans-4,5,13,14-tetradehydro-7a-homo-6α-PGI$_1$, a prostacyclin analog according to claim 46.

49. 16,16-Dimethyl-trans-4,5,13,14-tetradehydro-7a-homo-6α-PGI$_1$, a prostacyclin analog according to claim 46.

50. 16,16-Difluoro-trans-4,5,13,14-tetradehydro-7a-homo-6α-PGI$_1$, a prostacyclin analog according to claim 46.

51. A prostacyclin analog according to claim 43, wherein Z$_2$ is

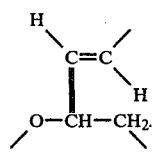

52. A prostacyclin analog according to claim 51, wherein Z$_1$ is —(CH$_2$)$_g$—CH$_2$—CF$_2$—.

53. 2,2-Difluoro-trans-4,5,13,14-tetradehydro-7a-homo-6β-PGI$_1$, a prostacyclin analog according to claim 52.

54. A prostacyclin analog according to claim 51, wherein Z$_1$ is —(CH$_2$)$_g$—CH$_2$—CH$_2$—.

55. A prostacyclin analog according to claim 54, wherein g is zero.

56. A prostacyclin analog according to claim 55, wherein R$_7$ is

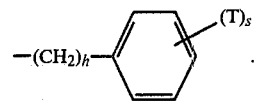

57. 17-Phenyl-18,19,20-trinor-trans-4,5,13,14-tetradehydro-7a-homo-6β-PGI$_1$, a prostacyclin analog according to claim 56.

58. A prostacyclin analog according to claim 55, wherein R$_7$ is

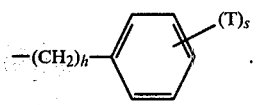

59. 16-Phenoxy-17,18,19,20-tetranor-trans-4,5,13,14-tetradehydro-7a-homo-6β-PGI$_1$, a prostacyclin analog according to claim 58.

60. A prostacyclin analog according to claim 55, wherein R$_7$ is —(CH$_2$)$_m$—CH$_3$.

61. A prostacyclin analog according to claim 60, wherein m is 3.

62. A prostacyclin analog according to claim 61, wherein R$_5$ is methyl.

63. 15-Methyl-trans-4,5,13,14-tetradehydro-7a-homo-6β-PGI$_1$, a prostacyclin analog according to claim 62.

64. A prostacyclin analog according to claim 61, wherein R$_5$ is hydrogen.

65. A prostacyclin analog according to claim 64, wherein at least one of R$_3$ and R$_4$ is fluoro.

66. 16,16-Difluoro-trans-4,5,13,14-tetradehydro-7a-homo-6β-PGI$_1$, a prostacyclin analog according to claim 65.

67. A prostacyclin analog according to claim 64, wherein at least one of R$_3$ and R$_4$ is methyl.

68. 16,16-Dimethyl-trans-4,5,13,14-tetradehydro-7a-homo-6β-PGI$_1$, a prostacyclin analog according to claim 67.

69. A prostacyclin analog according to claim 64, wherein R$_3$ and R$_4$ are both hydrogen.

70. Trans-4,5,13,14-tetradehydro-7a-homo-6β-PGI$_1$, methyl ester, a prostacyclin analog according to claim 69.

71. Trans-4,5,13,14-tetradehydro-7a-homo-6β-PGI$_1$, tris(hydroxymethyl)amino methane salt, a prostacyclin analog according to claim 69.

72. Trans-4,5,13,14-tetradehydro-7a-homo-6β-PGI$_1$, adamantanamine slat, a prostacyclin analog according to claim 69.

73. Trans-4,5,13,14-tetradehydro-7a-homo-6β-PGI$_1$, a prostacyclin analog according to claim 69.

* * * * *